United States Patent [19]

Shinohara et al.

[11] 4,284,486
[45] Aug. 18, 1981

[54] SOLID POLE OXYGEN SENSOR AND ITS MANUFACTURING PROCESS

[75] Inventors: Hiroshi Shinohara, Okazaki; Yasuhiro Otsuka, Toyota; Hideo Kamiya, Toyota; Hiroshi Wakizaka, Toyota; Toshinobu Furutani, Toyota, all of Japan

[73] Assignee: Toyota Jidosha Kogyo Kabushiki Kaisha, Aichi, Japan

[21] Appl. No.: 132,415

[22] Filed: Mar. 21, 1980

[30] Foreign Application Priority Data

Sep. 22, 1979 [JP] Japan .................. 54-122348

[51] Int. Cl.³ .................. G01N 27/58
[52] U.S. Cl. .................. 204/195 S; 29/592 R; 427/123; 427/125; 427/126.2; 427/126.3
[58] Field of Search .................. 204/195 S, 1 S; 427/123, 125, 126.2, 126.3; 422/98; 29/592 R

[56] References Cited

U.S. PATENT DOCUMENTS

| | | | |
|---|---|---|---|
| 4,208,265 | 6/1980 | Hori et al. | 204/195 S |
| 4,209,377 | 6/1980 | Shinohara et al. | 204/195 S |
| 4,209,378 | 6/1980 | Shinohara et al. | 204/195 S |

Primary Examiner—G. L. Kaplan
Attorney, Agent, or Firm—Stevens, Davis, Miller & Mosher

[57] ABSTRACT

A solid pole oxygen sensor wherein an oxygen sensor element is composed of a solid pole with one end of a lead wire buried therein; an internal electrode formed on the outside surface of the solid pole; a solid electrolyte enclosing the electrode to constitute a solid pole assembly as a column with a projection at its top; and a platinum electrode separated from the lead wire. The oxygen sensor element is so secured to an almost cylindrical ceramic insulator by means of adhesive or the like that the upper top side of the oxygen sensor element having the projection is matched to a recess at the tip of the cylindrical ceramic insulator and a pair of electroconductive zones provided on the side wall of the cylindrical ceramic insulator are electrically connected with the platinum electrode and the lead wire. A process of manufacturing a solid oxygen sensor is also disclosed.

32 Claims, 22 Drawing Figures

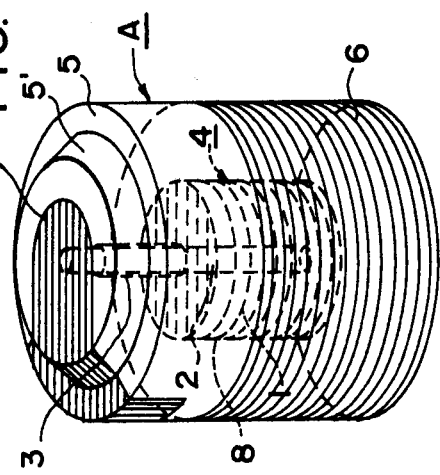
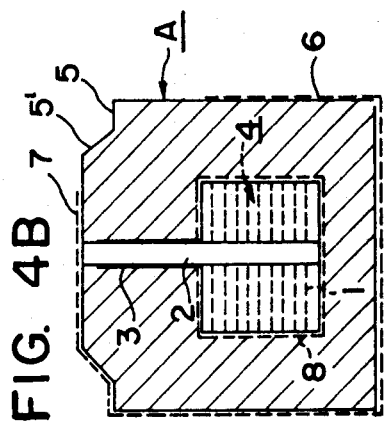
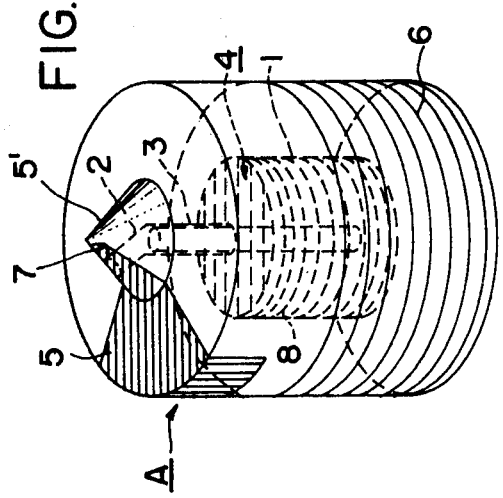
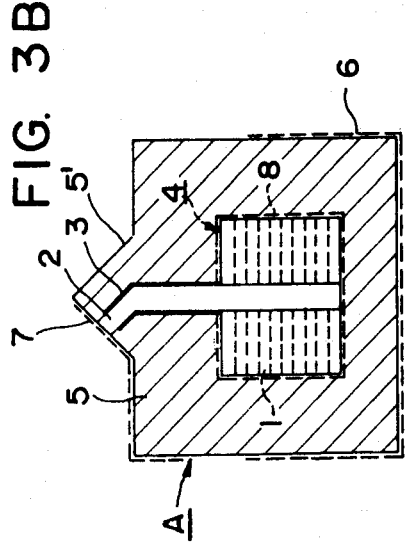

FIG. 6A
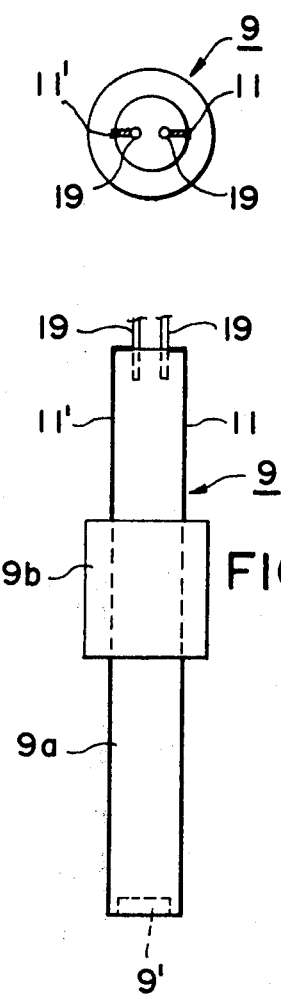
FIG. 6B
FIG. 6C
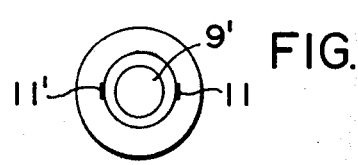
FIG. 7A
(NEGATIVE SIDE)
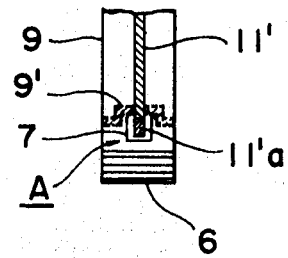
FIG. 7B
(POSITIVE SIDE)
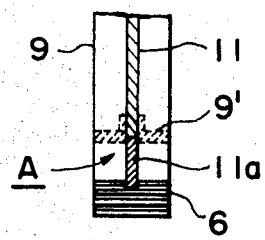

He DETECTION

SOLID POLE OXYGEN SENSOR AND ITS MANUFACTURING PROCESS

BACKGROUND OF THE INVENTION (1) Field of the Invention

The present invention relates to a solid pole oxygen sensor, and more particularly to a solid pole oxygen sensor which is to be set in an automotive exhaust system to detect the oxygen concentration in the exhaust gas, and to a process of manufacturing such a solid pole oxygen sensor.

(2) Description of the Prior Art

An oxygen sensor is a device for measuring the equilibrium oxygen partial pressure in a gas to be measured and it is conventionally constituted such that internal and external electrodes of platinum or platinum family alloy film are formed inside and outside of a solid electrolyte vessel made of a solid electrolyte such as zirconia which is usually stabilized with, for instance, yttrium oxide. The vessel is filled with air (gas) of a solid substance with a constant equilibrium oxygen partial pressure, for instance, a mixed powder of metal-metal oxide as the internal reference material; and thereby the equilibrium oxygen partial pressure of the gas to be measured can be detected by converting the ratio of the equilibrium oxygen partial pressures between the gas and the internal reference material to an electromotive force. As the internal reference material, gases and solids are available. However, because the oxygen sensor is to be positioned in an automobile, a solid is found more advantageous from the standpoint of physical properties and structure.

The conventional solid pole oxygen sensor, which requires calcinating or high-temperature firing of the solid electrolyte vessel in its manufacture, is troublesome. It is too complicated structurally to be reduced in dimensions. Moreover, it is difficult to take out the potential of the internal electrode in the solid electrolyte vessel.

SUMMARY OF THE INVENTION

The primary object of the present invention is to provide a solid pole oxygen sensor having simplified and miniaturized structure and designed to easily take out the potential of an oxygen sensor.

Another object of the present invention is to provide a solid pole oxygen sensor which is simple and fit for miniaturization and a process of manufacturing such a solid pole oxygen sensor wherein the solid pole oxygen sensor element is designed as a column with a projection at the top and the projection is fitted into a recess at the tip of a ceramic insulator and joined thereto.

Still another object of the present invention is to provide a process of manufacturing a solid pole oxygen sensor comprising the steps of:

forming a solid pole by burying one end of a lead wire in a powder mixture with the other end of it exposed above the powder mixture and sintering it;

forming an internal electrode on the outside surface of the solid pole in such a manner that it may be electrically connected to the lead wire;

enclosing the solid pole in a solid electrolyte simultaneously by forming a projection on the top side of the solid electrolyte and sintering it with the other end of the lead wire faced or flush with the outside surface of the solid electrolyte, thereby constituting a column of solid electrolyte internally holding a solid pole;

forming an external electrode on the outside surface of the column to complete an oxygen sensor element;

forming a ceramic insulator with a recess formed on the bottom side thereof;

forming one electroconductive zone and another electroconductive zone which is not conductive to the former on the side surface of the ceramic insulator;

fitting the oxygen sensor element to said insulator, so that the first electroconductive zone may be electrically connected with the exposed end of the lead wire, and the second electroconductive zone may be electrically connected with the external electrode, and the oxygen sensor element may be fixed by inserting the projection formed on the top side of the oxygen sensor element into the recess formed on the bottom side of the ceramic innsulator.

Still another object of the present invention is to provide a solid pole oxygen sensor which comprises:

a lead wire;

a solid pole in which one end of the lead wire is buried and above which the other end of the lead wire is exposed;

an internal electrode formed on the outside surface of the solid pole and electrically connected to the lead wire;

a solid electrolyte which encloses the solid pole and the lead wire with the other end of the lead wire located facing outside and with a projection formed on the top side of the solid electrolyte;

an external electrode formed on the outside surface of the solid electrolyte; and a ceramic insulator having a recess formed on the bottom side thereof and one electroconductive zone and another electroconductive one spaced therefrom and nonconductive thereto, wherein the recess is mated with the projection and the projection is inserted into the recess and fixed therein; the first electroconductive zone on the ceramic insulator is electrically connected to the lead wire, and the second electroconductive zone on the ceramic insulator is electrically connected to the external electrode.

Still another object of the present invention is to provide a solid pole oxygen sensor characterized by easiness of assembling in that the profile of a recess at the tip of the ceramic insulator matches the profile of a projection on the oxygen sensor element which is to be joined with the ceramic insulator; and a process of manufacturing this solid pole oxygen sensor.

Still another object of the present invention is to provide a solid pole oxygen sensor with durability increased through coating its lead wire with a sealing material; and the process of manufacturing this solid pole oxygen sensor.

Other objects of the present invention will become apparent from the following detailed description of it.

BRIEF DESCRIPTION OF THE DRAWINGS

FIG. 3A is a perspective view illustrating another embodiment of the oxygen sensor element according to the present invention and FIG. 3B is a sectional view of FIG. 3A;

FIG. 4A is a perspective view illustrating still another embodiment of the oxygen sensor element according to the present invention and FIG. 4B is a sectional view of FIG. 4A;

FIG. 6A is a plan view of a ceramic insulator, FIG. 6B is a front elevation view, and FIG. 6C is a bottom view;

FIG. 7A is a negative-side view of the insulator and the oxygen sensor element connected thereto, and FIG. 7B is a positive-side view;

DETAILED DESCRIPTION OF THE PREFERRED EMBODIMENTS

Figure 1A:
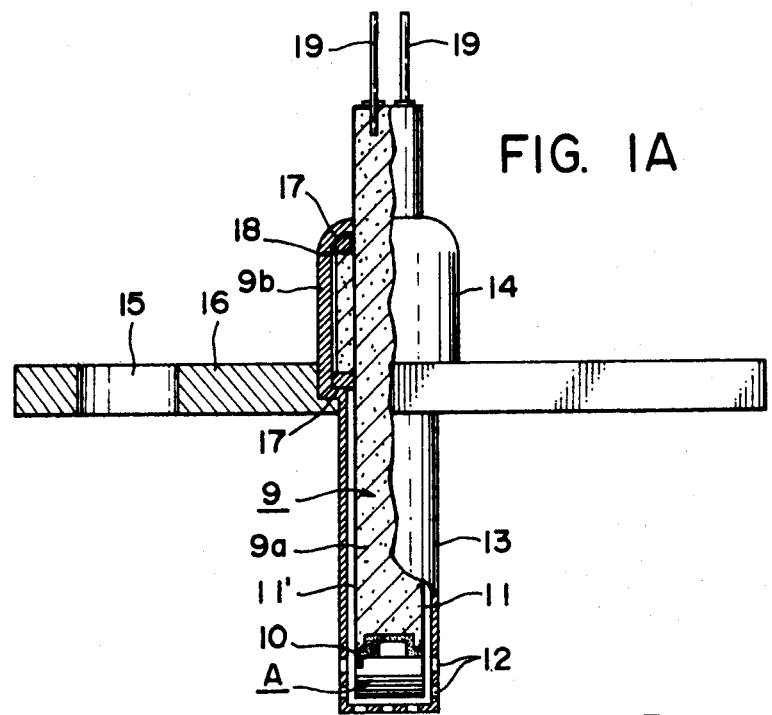
FIG. 1A is a side view partly in section view of a solid pole oxygen sensor according to the present invention.
Figure 1B:
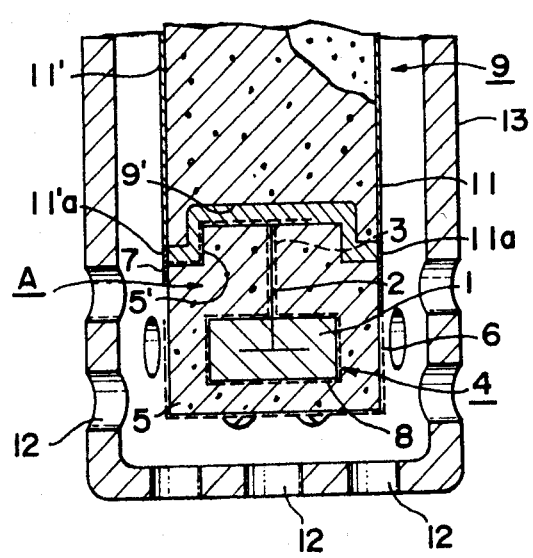
FIG. 1B is an enlarged sectional side view of the tip of the solid pole oxygen sensor shown in FIG. 1A.

Referring to the attached drawings, the embodiments of the present invention will now be described. In FIGS. 1A and 1B, one end of a fine lead wire 2 made of platinum or platinum-rhodium is buried in a solid pole 1 made of a metal-metal oxide powder. The exposed part of the lead wire 2 is coated with a sealing material 3; and an internal electrode 8 (negative-side) is formed on the surface of the solid pole 1, thus constituting a solid pole assembly 4.

The solid pole assembly 4 is enclosed in a solid electrolyte 5 which is molded by compression into a column with a projection 5' at the top; dried and then fired in a reducing atmosphere; and by means of plating or baking, a positive and a negative (auxiliary) electrode are formed on the surface of the column, thus constituting an oxygen sensor element A.

A ceramic insulator 9 to which the oxygen sensor element A is to be joined will now be described with the reference to the drawings.

Two platinum electroconductive zones 11, 11' are formed to diametrically oppose each other over the entire length of the side wall of a slender cylindrical body 9a of the ceramic insulator 9 and a ring 9b is inserted into and fixed to the body 9a for housing it in a holder. The platinum electroconductive zones 11, 11' are provided respectively for connection to the positive electrode 6 and the negative auxiliary electrode 7.

The ceramic insulator 9 and the oxygen sensor element A are integrally joined by means of an adhesive 10, with the projection 5' of the element A engaging the recess 9' at the tip of the insulator 9. Sealers 11a, 11'a made of an electroconductive material are provided between the conductive zones 11, 11' and the electrodes 6, 7 of the element A for electrical connection therebetween. Then, the surface of the oxygen sensor element may be provided with a spinel coating layer of $MgAl_2O_4$ (50-150 u) (not shown) which is formed by plasma spray coating.

The integrated assembly of the element A and the insulator 9 is then placed within a protective cover 13 with ventilation holes 12 and a housing 14; and it is mounted approximately at midpoint of a flange 16 having fitting holes 15.

Also shown in the drawings are a metal packing 17, a filler 18 and two lead wires 19.

The solid pole 1 in the oxygen sensor element according to the present invention is made of a mixed powder of a metal-metal oxide, for instance Co/CoO, V/VO, Fe/FeO, which is added with appropriate volumes of other substances such as an anti-sinter agent, and/or a porosity agent. As the anti-sinter agent, the same substances as the solid electrolyte, e.g., $ZrO_2$ stabilized with $Y_2O_3$, is recommended. As the porosity agent, a substance which sublimates at a low temperature of less than 100° C. is available. For instance, when the solid pole is Fe/FeO, the composition will be 45 weight % of Fe (carbonium iron decomposed powder), 10 weight% of $ZrO_2$ containing 5.5 mol % $Y_2O_3$ and 45 weight % of $NH_4HCO_3$ (porosity agent). For the purpose of improving the activity of the solid pole, it is advisable to add to the above-mentioned mixture a small amount of platinum black, for instance, 2 weight %, as the activating agent.

The lead wire 2 is desirably as fine as possible insofar as it is not liable to snap, for instance, 0.05-0.5 mm$\phi$, preferably 0.05-0.2 mm $\phi$. If the wire is thick, the surface area of it will increase, resulting in a poor sinterability of the surrounding solid electrolyte. If, however, the wire is too fine, such a phenomenon will not occur, but the wire may snap. The lead wire 2 is made of platinum or platinum/rhodium. When it is made of platinum/rhodium, the rhodium is desirably 10-35 weight % of platinum. The optimum ratio is 15-25 weight %.

At less than 10 weight %, the heat resistance is poor and the wire is likely to snap. At more than 35 weight %, the durability is good by the workability will drop because of decreased flexibility of the wire.

A sealing material 3 is provided around a part or the whole part of the exposed portion of the lead wire 2, one end of which is buried in the solid pole 1, or near the tip of the exposed part of the lead wire. The sealing material 3 is composed of an electroconductive metal such as platinum or platinum-rhodium alloy and an organic binder. It is for instance composed of an organic binder such as ethylcellulose+butylcarbitolacetate (BCA) or nitrocellulose+butyl acetate, and more than 15 weight %, desirably 15-20 weight %, of platinum. It is recommended that a nitrocellulose base binder, which is easy to eliminate by heating, be used. A glass-based sealer used to be employed for sealing the solid pole oxygen sensor, but because of gas leak or poor sealing effect revealed in a high-temperature durability test, it has been found to be less desirable. According to the present invention in which an electroconductive paste of metal such as platinum metallizer is employed as the sealer, an excellent sealing effect is obtained with no gas leak and no poor sealing in a high-temperature durability test.

The solid electrolyte 5 is $ZrO_2$ added with 4-10 mol % of $Y_2O_3$. From the standpoint of heat shock, use of a partially stabilized $ZrO_2$ is recommended; and for the purpose of low temperature firing, use of $ZrO_2$ with a low mol % of $Y_2O_3$ is desirable.

The anti-sintering agent to be added to the solid pole should be the same substance as the solid electrolyte used here.

For formation of the oxygen sensor element a solid pole assembly 4 enclosed in a solid electrolyte 5 is pressed in a specified metal mold by a hand-press or the like, the molding pressure being desirably 600–2,000 kg/cm$^2$. At more than 2,000 kg/cm$^2$m, the air cannot be sufficiently extracted out of the molded product and, as a result, air bubbles remain in the sintered product, which is undesirable.

The sensor element A formed with a projection is dried for 15–30 minutes at 200° C. in the atmosphere to dissipate the organic binder in the sealer 3. The drying temperature in this oxidizing atmosphere should be up to 300° C. at most. If the molding pressure is reduced, naturally the drying time can be shortened. The molding pressure can be reduced up to 100 mmHg at most; an over reduction will not be useful, because it causes a deformation in the molded product.

Firing is done in an electric furnace for 2–3 hours at 1350°–1500° C. in a reducing atmosphere of inert gas such as Ar, N$_2$ added with a small amount (0.5–2 Vol %) of a reducing gas, such as H$_2$. The higher the firing temperature the better, but a temperature below the sintering temperature of the solid pole is desirable considering prevention of sintering and grain growth of the solid pole and deterioration of the lead wire. When all things are considered, the above-mentioned range of temperatures would be optimum. To be more specific, the temperature should be one at which the solid pole does not sinter too hard or at which the metal in the solid pole does not melt. The sintering time differs depending on the kind of solid electrolyte used, but the sintering treatment should be executed until the water-absorption rate according to JIS (Japan Industrial Standard) R 2205 becomes equal to 0%. Thereby it is not desirable for sinterability that the temperature rise take place in a short time. The optimum temperature-rise rate would be 100°–300° C./hr.

The positive electrode 6 and the negative auxiliary electrode 7 formed on the surface of the solid electrolyte 5 are made of platinum alone or a mixture of platinum and a different element in the platinum family. They can be formed by platinum plating, platinum paste coating/baking, platinum printing/baking, chloroplatinic acid baking, or ion plating; among them, the plating method is the most desirable. The negative (solid pole) electrode 8 formed on the periphery of the solid pole assembly 4 is made of the same material as the sealer 3.

Methods of forming electrodes on the oxygen sensor element wll now be described.

a. Example of platinum plating

| | |
|---|---|
| Pretreatments: | |
| etching (with hydrofluoric acid) | 30 minutes |
| ultrasonic washing (with distilled water) | 3 minutes |
| immersion in platinum containing solution | 10 minutes |
| drying at room temperature | 8 hours |
| Surface reduction (with commercial reducing agent) | 10 minutes |
| Chemical plating with platinum up to surface resistance | 5Ω |
| Electroplating with platinum | below 1Ω at film thickness of 1μ | b. Example of chloroplatinic acid baking

The element is immersed in a butylcarbitol solution of chloroplatinic acid, lifted out of the solution, and then dried. The immerse-dry cycle is repeated until the surface resistance becomes equal to about 1Ω.

c. Example of platinum paste coating and baking

A commercial platinum paste (e.g., Product No. 8105 manufactured by Kabushiki Kaisha Tokuriki Kagaku Kenkyujo) is evenly spread over a pretreated (degreased) surface of the oxygen sensor element. After drying, baking is done in the atmosphere at 950° C. for 10 minutes.

Figure 2A:
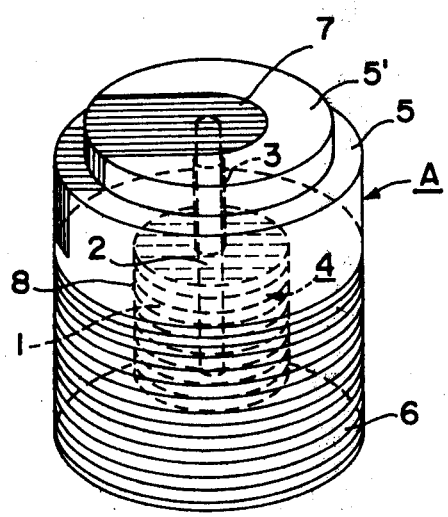
FIG. 2A is a perspective view of an oxygen sensor element according to the present invention.
Figure 2C:
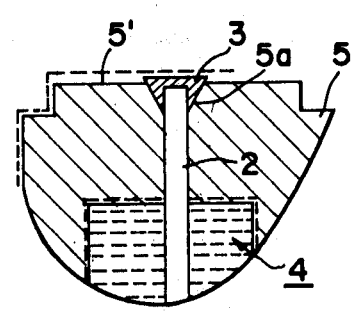
FIG. 2B is a sectional view of FIG. 2A, and FIGS. 2C and 2D are respectively sectional views illustrating the lead wire being coated with a sealing material in other embodiments of the invention.
Figure 2B:
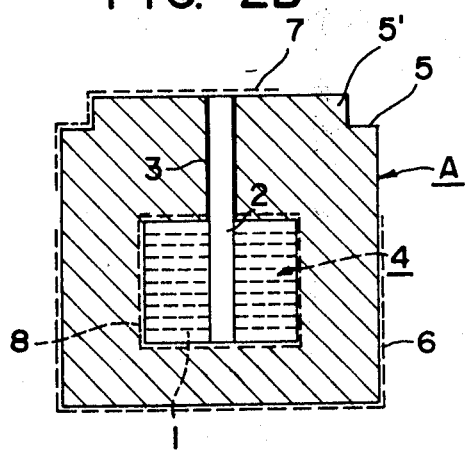

An embodiment of the oxygen sensor element A according to the present invention is illustrated in FIGS. 2A and 2B. In the following examples, like parts are denoted by like symbols. In this embodiment, the lead wire 2 is buried in the solid pole 1 (better results will be obtained when the tip of the buried lead wire 2 is curved in a circular form to suit the profile of the solid pole 1). Said circular form may be made parallel to the bottom surface of the solid pole. A negative electrode 8 is formed on the outside surface of the solid pole 1 and a sealing material 3 is spread on the surface of the exposed lead wire 2, thus constituting a solid pole assembly 4. The solid pole assembly 4 is enclosed in a solid electrolyte 5 and pressed into a column with a disc-like projection 5'. Thereafter, the electrodes 6 and 7 are formed through given operations.

Figure 2D:
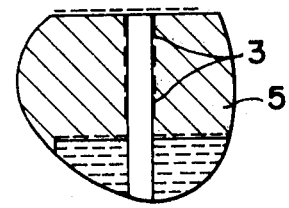
Figure 5A:
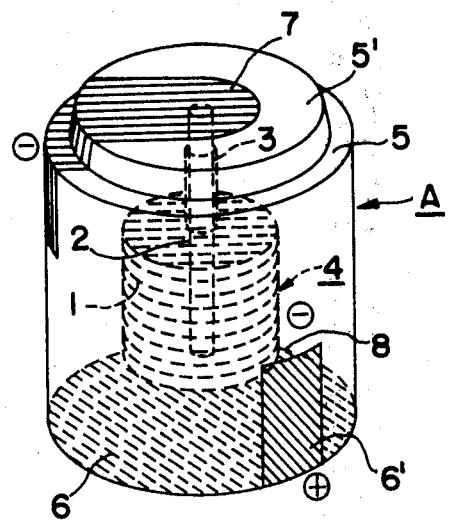
FIG. 5A is a perspective view showing an area of the oxygen sensor element where the electrodes are formed.
Figure 5C:
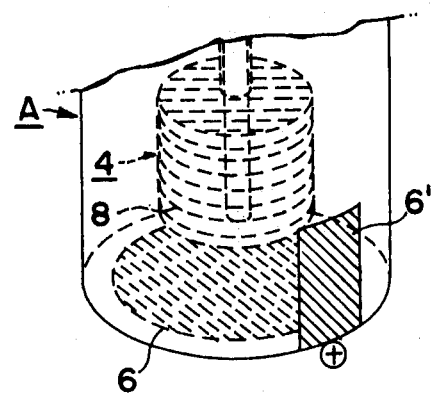
FIG. 5C is a fragmentary perspective view of a different embodiment.
Figure 5B:
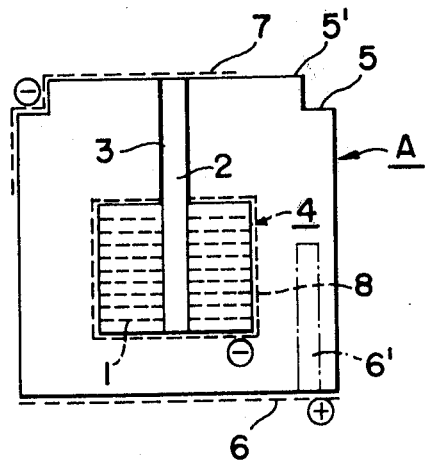
FIG. 5B is a sectional view of FIG. 5A.
Figure 5D:
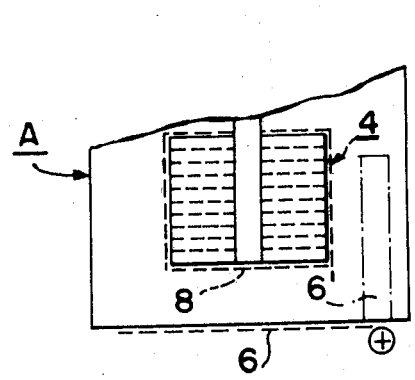
FIG. 5D is a sectional view of FIG. 5C.

The sealing material 3 thereby may be spread to cover the whole surface or only a partial surface of the exposed lead wire 2 (FIGS. 2B and 2D).

Or as indicated in FIG. 2C, a part on the lead wire 2 of the solid pole assembly 4 as enclosed in the solid electrolyte 5 is pared off to produce a recess 5a with a coarse surface or so molded to produce such a recess with a coarse surface, thereby exposing a small portion of the lead wire 2; and then sintering is effected so that the recess 5a is filled up with a conductive paste sealer 3 or not filled therewith. In the former case, the electrodes are formed in the same way as above; and in the latter case, the electrodes are formed in the same way as above, after the recess 5a is filled with the electroconductive sealer 3, which is then baked. It goes without saying that the sealing is done as shown in FIGS. 2C and 2D.

Another embodiment of the oxygen sensor element A according to the present invention will now be described.

The one shown in FIGS. 3 and 4 is designed as a truncated cone, with the structure and function being the same as in FIG. 2. When the projection 5' is conical, it would be advisable to direct the upper end of the lead wire toward the cone. The projection may be designed pyramidal. Furthermore, the projection 5' may be formed as a square pillar. The electrode to be formed on the surface of the solid electrolyte 5 may be designed as the positive electrode, with the negative auxiliary electrode 7 being provided at the junction to the lead wire 2. Therefore, the areas for forming the positive electrode 6 and the negative auxiliary supplemental electrode 7 are not limited to the areas indicated in FIGS. 2, 3, and 4. For instance, as illustrated in FIG. 5, the electrode 6 may be formed only at the base of the oxygen sensor element, one part 6' of it being formed in rectangular shape on the side surface of the element.

Next, the ceramic insulator, to which the oxygen sensor element A is to be joined, will be described with reference to FIG. 6.

As shown in the drawing, the insulator 9 used in the present invention has a pair of platinum electroconductive zones 11, 11' formed over the entire length on the side wall of its approximately columnar, for instance, cylindrical body 9a. These zones 11, 11' are formed by platinum paste baking or platinum print baking. A recess 9' is provided at the bottom of the tip of the insulator 9 to receive and join the sensor element A. At the top of the electroconductive zones 11, 11', two lead wires 19 of Inconel (for instance, Inco 600 or 610) are laser-welded.

An example of joining the oxygen sensor element to the insulator 9 is shown in FIG. 7, in which it is seen that the end of the negative auxiliary electrode 7 of the oxygen sensor element A is brought into contact with the recess 9' of the insulator 9 and the side walls with the electrodes 6, 7 are aligned with the electroconductive zones 11, 11'. In this arrangement, the joining is made by use of the adhesive 10. One electroconductive zone 11' is connected to the negative auxiliary electrode 7 of the sensor element A, while the other electroconductive zone 11 is connected to the positive electrode 6; and thereby electroconductive materials 11a, 11'a, such as platinum paste, are spread and baked to ensure the connection between the electroconductive zones 11, 11' and the electrodes 6 and 7 of the sensor element A.

At strategic points of the oxygen sensor insulating spinel coatings of 10–20μ are provided to prevent snapping of the electroconductive zones 11, 11'; separation of the electronconductive zones from the insulator; short circuiting of the electroconductive zones to the holder; breaking of the electroconductive materials 11a, 11'a; separation of joined surfaces of the electroconductive zones; short circuiting of them to the holder; and separation of the positive electrode in the oxygen sensor element.

The ceramic insulator 9 is made of an insulating material such as spinel like $Al_2O_3$ or $MgO.Al_2O_3$, forsterite, or mullite.

As the adhesive, the following materials are desirable: $CaO-Al_2O_3-MgO$ base-, $SiO_2-CaO-Al_2O_3$ base-, $SiO_2-CaO-Al_2O_3-MgO$ base-, $SiO_2-Al_2O_3-Na_2O$ base-, $SiO_2-MgO$ base-, $TiO_2-BaO$ base-, $SiO_2-Al_2O_3-ZrO_2-Na_2O$ base- adhesive, or the like.

The components of the holder for the solid pole oxygen sensor according to the present invention, i.e., the protective cover 13, the housing 14 and the flange 16 are made of stainless steel. The insulator is fastened to the holder by caulking at 600° C. in the air. The metal packing 17 consists of a stainless steel or copper-made ring. The filler 18 is graphite, asbestos or pyrophyllite.

When the automotive exhaust system is equipped with a solid pole oxygen sensor according to the present invention, the exhaust gas flowing through the exhaust system comes into contact with the oxygen sensor element A through the ventilation hole 12 of the protective cover 13 and thereby an electromotive force is generated due to a difference between the equilibrium oxygen partial pressure $P_{O2}$ of the solid pole 1 and the oxygen partial pressure $P'_{O2}$ in the exhaust gas. Measurement of this electromotive force gives the oxygen concentration at the part to be measured.

The partial pressure ratio and the electromotive force are in the following relationship:

$$E = \frac{RT}{nf} \ln \frac{P'_{O2}}{P_{O2}}$$

where

R: gas constant
T: absolute temperature
F: Faraday constant

A solid pole oxygen sensor according to the present invention was set in an automotive exhaust system and durability tests were performed on 10 modes of running patterns for evaluation of the performance of the solid pole oxygen sensor. Evaluation was made by the helium leak test, conductivity test, autoclave test, response test and appearance test.

Helium leak test

Figure 8:
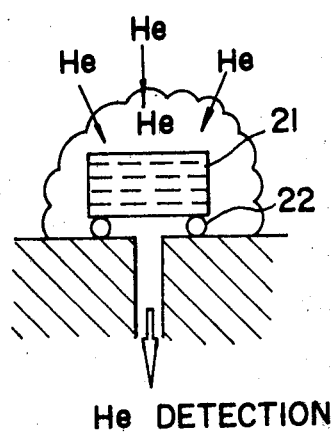
FIG. 8 is a diagram showing an He leak test.

The sample 21 (oxygen sensor element) was mounted on an O-ring (silicone rubber+silicone grease) 22, as shown in FIG. 8; and He gas was blasted around it. In this condition, evacuation was done in the direction of the arrow and thereby the He gas concentration in the extracted gas was analysed by the He detector to estimate the gas-tightness of the element itself.

Autoclave test

Figure 9:
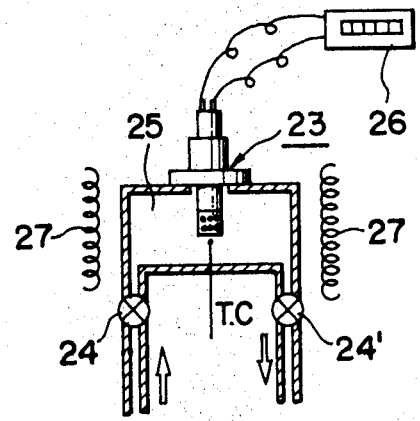
FIG. 9 is a diagram illustrating an autoclave test.

As indicated in FIG. 9, a solid pole oxygen sensor 23 according to the present invention was set at midpoint of a tube 25 with both ends sealed by the electromagnetic valves 24, 24'. A d-c voltmeter 26 was connected to the oxygen sensor 23, and a heater was set around the tube 25. In this arrangement the atmosphere in the tube 25 was kept at 500° C. by the heater 27. Then, from one of the valves 24, the air was pressurized to, for instance, 5 kg/cm². A change in the electromotive force was thereby detected by the d-c voltmeter 26. Normally, the pressurization results in a wide difference of the oxygen partial pressure and in an increased electromotive force. However, the electromotive force will drop if the sealing is poor or the deterioration is heavy.

Response test

Figure 10:
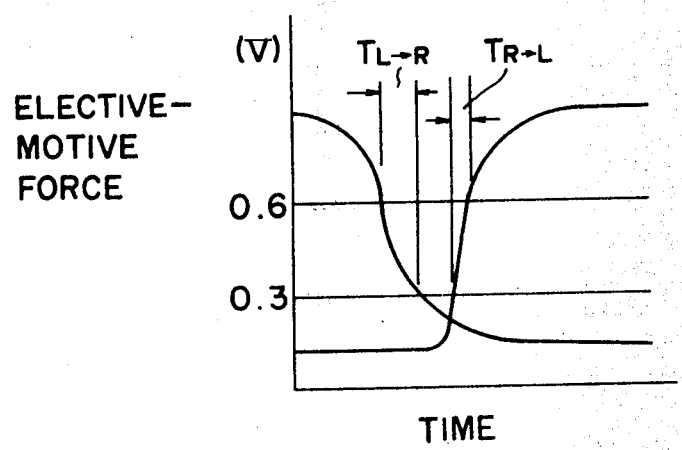
FIG. 10 is a diagram illustrating the response characteristics of the oxygen sensor.

FIG. 10 is a diagram illustrating the response characteristics of the solid pole oxygen sensor against the oxygen concentration of the exhaust gas. The time taken for the electromotive force to change from 0.3 V to 0.6 V under the engine burning conditions, from rich to lean (R→L) or from lean to rich (L→R), is respectively put as $T_{R \to L}$ or $T_{L \to R}$. Generally speaking, the solid pole oxygen sensor suffers deterioration after a durability test; namely $T_{R \to L}$ and $T_{L \to R}$ are retarded. The best condition is that both $T_{R \to L}$ and $T_{L \to R}$ are fast and the change after the durability test is little.

The test results of the solid pole oxygen sensor according to the present invention are summarized in Table 1.

TABLE 1

| | Test items | | | | | | | | |
|---|---|---|---|---|---|---|---|---|---|
| | He leak | | | Autoclave | | | Response | | |
| | Durability (hrs.) | | | | | | | | |
| Element | 0 | 200 | 500 | 0 | 200 | 500 | 0 | 200 | 500 |
| 1 | O | O | O | O | O | O | O | O | O |
| 2 | O | O | O | O | O | O | O | O | O |
| 3 | O | O | O | O | O | O | O | O | O |
| 4 | O | O | O | O | O | O | O | O | Δ |

Notes:
O good
Δ poor
X unfit for service (deteriorated)

As described above, according to the present invention, the whole structure of a solid pole oxygen sensor can be simplified, because the oxygen sensor element is designed as a column with a projection at the top and the projection is fitted into a recess at the tip of the insulator and fixed there.

Since the solid pole oxygen sensor is assembled with a pair of electroconductive zones on the insulator connected to a pair of electrodes on the oxygen sensor element, the connection of electrodes is easy.

Moreover, if the lead wire is coated with a sealing material, the sealing material will serve to mitigate the boundary strain due to a difference in thermal expansion between the solid electrolyte and the lead wire, thereby enhancing the durability of the solid electrolyte.

We claim:

1. A process of manufacturing a solid pole oxygen sensor, said process comprising the steps of:
    forming a solid pole by burying one end of a lead wire in a powder mixture and sintering it with the upper end of the wire exposed thereabove;
    forming an internal electrode on the outside surface of said solid pole with said internal electrode electrically connected to said lead wire;
    enclosing said solid pole in a solid electrolyte with the upper end of said lead wire connected to the outside surface of said solid electrolyte and sintering it, thereby constituting a column of solid electrolyte having a projection on the top side thereof and internally holding a solid pole;
    forming an external electrode on the outside surface of said column, thereby completing an oxygen sensor element;
    forming on the side surface of a ceramic insulator with a recess formed in the bottom thereof, one electroconductive zone and another electroconductive zone being nonconductive to the former; and
    attaching and joining said oxygen sensor element to said insulator in such a manner that said oxygen sensor element is attached to said insulator, with the projection mating with said recess so that said first electroconductive zone may be electrically connected to the upper end of said lead wire and said second electroconductive zone may be electrically connected to said external electrode.

2. A process as claimed in claim 1, wherein said projection on the element is a truncated cone and said recess in the insulator is designed to have a matching profile.

3. A process as claimed in claim 1, wherein said projection is conical and said recess is designed to have a matching profile.

4. A process as claimed in claim 3, wherein the upper end of said lead wire is exposed on the surface of said cone.

5. A process as claimed in claim 1, wherein one part of said lead wire is coated with a sealing material, thereby isolating said lead wire from said solid electrolyte.

6. A process as claimed in claim 5, wherein said sealing material is composed of an electroconductive metal and an organic binder.

7. A process as claimed in claim 6, wherein said organic binder is a nitrocellulose base compound.

8. A process as claimed in claim 6, wherein said organic binder is an ethylcellulose base compound.

9. A process as claimed in claim 6, wherein said electroconductive metal is platinum.

10. A process as claimed in claim 1, wherein the oxygen sensor element and the insulator are joined by an adhesive.

11. A process as claimed in claim 10, wherein said adhesive is one selected from $CaO-Al_2O_3-MgO$ base-, $SiO_2-CaO-Al_2O_3$ base-, $SiO_2-CaO-Al_2O_3-MgO$ base-, $SiO_2-Al_2O_3-Na_2O$ base-, $SiO_2-MgO$ base-, $TiO_2-BaO$ base-, and $SiO_2-Al_2O_3-ZrO_2Na_2O$ base- adhesive.

12. A process as claimed in claim 1, wherein the oxygen sensor element is supplemented with a third electrode extending from the top to the side of the oxygen sensor element to electrically connect the first electroconductive zone to the lead wire.

13. A process as claimed in claim 1, wherein the external electrode of the oxygen sensor element is formed on the bottom of said element.

14. A process as claimed in claim 1, wherein the lead wire is substantially straight.

15. A process of manufacturing a solid pole oxygen sensor, said process comprising the steps of:
    forming a solid pole by burying one end of a lead wire in a powder mixture and sintering it with the upper end of the lead wire exposed thereabove;
    forming an internal electrode on the outside surface of the solid poly with the internal electrode electrically connected to the lead wire;
    compression molding a solid electrolyte into a substantially cylindrical shape, with a projection circular in transverse cross-section and of small diameter, on the top, with the upper end of the lead wire connected to the outside surface of the solid electrolyte;
    forming an external electrode on the outside surface of the solid electrolyte to produce an oxygen sensor element;
    forming on the cylindrical side surface of a substantially cylindrical ceramic insulator with a recess, circular in transverse cross-section and of complementary shape to that of the projection, in the bottom thereof, a first longitudinally extending electroconductive zone and a second longitudinally extending electroconductive zone diametrically opposed to and nonconductive with the first zone; and
    adhesively securing the projection on the oxygen sensor element into the recess on the insulator with the first electroconductive zone electrically connected to the upper end of the lead wire and the second electroconductive zone electrically connected to the external electrode.

16. A process of manufacturing a solid pole oxygen sensor, said process comprising the steps of:
    forming a solid pole by burying one end of a lead wire in a powder mixture and sintering it with the upper end of the lead wire exposed thereabove;
    forming an internal electrode on the outside surface of the solid pole with the internal electrode electrically connected to the lead wire;
    compression molding under a pressure of 600 to 2000 $kg/cm^2$ a solid electrolyte into a substantially cylindrical shape, with a projection, circular in transverse cross-section and of smaller diameter, on the top, about the solid pole with the upper end of the lead wire connected to the outside surface of the solid electrolyte;
    drying the compression molded solid electrolyte with the solid pole therein for 15 to 30 minutes at about 200° C. in the atmosphere;
    firing the compression molded solid electrolyte with the solid pole therein for 2 to 3 hours at 1350° to 1500° C. in a reducing atmosphere of inert gas;

forming an external electrode on the outside surface of the solid electrolyte to produce an oxygen sensor element;

forming on the cylindrical side surface of a substantially cylindrical ceramic insulator with a recess, circular in transverse cross-section end of complementary shape to that of the projection, in the bottom thereof, a first longitudinally extending electroconductive zone and a second longitudinally extending electroconductive zone diametrically opposed to and nonconductive with the first zone; and adhesively securing the projection on the oxygen sensor element into the recess on the insulator with the first electroconductive zone electrically connected to the upper end of the lead wire and the second electroconductive zone electrically connected to the external electrode.

17. A solid pole oxygen sensor comprising:
a lead wire;
a solid pole with one end of said lead wire buried therein, the other end of the wire being exposed;
an internal electrode on the outside surface of said solid pole and electrically connected to said lead wire;
a solid electrolyte enclosing said solid pole and being connected to the other end of said lead wire at its outer surface;
an external electrode on the outside surface of said solid electrolyte;
a ceramic insulator having formed thereon one electroconductive zone and another electroconductive zone spaced therefrom and nonconductive thereto:
a projection on the top of said solid electrolyte;
a recess, of profile matching that of the projection, on the bottom of the ceramic insulator;
said projection being fitted into said recess for joining the element and the insulator; and,
the first electroconductive zone on the insulator is connected to the lead wire, and the second electroconductive zone is connected to the external electrode.

18. A solid pole oxygen sensor as claimed in claim 17, wherein the projection on the element is a truncated cone, and the recess in the insulator has a profile to match the truncated cone of the projection.

19. A solid pole oxygen sensor as claimed in claim 17, wherein said projection is a cone, and said recess has a profile to match the cone.

20. A solid pole oxygen sensor as claimed in claim 19, wherein the other end of the lead wire is exposed on the surface of said cone.

21. A solid pole oxygen sensor as claimed in claim 20, wherein one part of the lead wire is coated with a sealing material, thereby isolating the lead wire from the solid electrolyte.

22. A solid pole oxygen sensor as claimed in claim 21, wherein the sealing material is composed of an electroconductive metal and an organic binder.

23. A solid pole oxygen sensor as claimed in claim 22, wherein the organic binder is a nitrocellulose base compound.

24. A solid pole oxygen sensor as claimed in claim 22, wherein the organic binder is an ethylcellulose base compound.

25. A solid pole oxygen sensor as claimed in claim 22, wherein the electroconductive metal is platinum.

26. A solid pole oxygen sensor as claimed in claim 17, further comprising an adhesive for joining the element to the insulator.

27. A solid pole oxygen sensor as claimed in claim 26, wherein the adhesive is one selected from among $SiO_2$-$CaO$-$Al_2O_3$ base-, $SiO_2$-$CaO$-$Al_2O_3$-$MgO$ base-, $SiO_2$-$Al_2O_3$-$Na_2O$ base-, $SiO_2$-$MgO$ base-, $TiO_2$-$BaO$ base- and $SiO_2$-$Al_2O_3$-$ZrO_2$-$Na_2O$ base- adhesive.

28. A solid pole oxygen sensor as claimed in claim 17, wherein the auxiliary electrode to electrically connect the first conductive zone to the lead wire is extended from the top to the side of the solid electrolyte.

29. A solid pole oxygen sensor as claimed in claim 17, wherein the external electrode of the solid electrolyte is on the bottom of the solid electrolyte, and the internal electrode of the solid pole is on the bottom of the solid pole.

30. A solid pole oxygen sensor as claimed in claim 17, wherein the lead wire is substantially straight.

31. A solid pole oxygen sensor as claimed in claim 17, wherein the portion of the lead wire buried in the solid pole is curved in a circular to suit the profile of the solid pole.

32. A solid pole oxygen sensor comprising:
a lead wire;
a solid pole, one end of said lead wire being buried in said solid pole and the other end thereof being exposed exterior of said solid pole;
an internal electrode on the outside surface of said solid pole and externally connected to the lead wire;
a solid electrolyte enclosing said solid pole, said electrolyte being substantially cylindrical with a centrally disposed projection, of circular transverse cross-section and smaller diameter, on the top thereof, the upper outside surface of said projection being connected to the other end of said lead wire;
an external electrode on the outside surface of the solid electrolyte;
a substantially cylindrical ceramic insulator having a first longitudinally extending electroconductive zone thereon and a second longitudinally extending electroconductive zone thereon, said second zone being diametrically opposed to and nonconductive with said first zone, said first zone being connected to the lead wire and said second zone being connected to the external electrode, means defining a centrally disposed recess, circular in transverse cross-section and of complementary shape to that of the projection cross-section in the bottom of the insulator, said projection being adhesively secured within said recess.

* * * * *